US00PP21278P2

(12) United States Plant Patent
Lemon

(10) Patent No.: US PP21,278 P2
(45) Date of Patent: Sep. 7, 2010

(54) ***GERANIUM* PLANT NAMED 'OGLREG3067'**

(50) Latin Name: *Pelargonium×domesticum*
Varietal Denomination: Oglreg3067

(75) Inventor: David G. Lemon, Lompoc, CA (US)

(73) Assignee: Ecke Geraniums LLC, Encinitas, CA (US)

( * ) Notice: Subject to any disclaimer, the term of this patent is extended or adjusted under 35 U.S.C. 154(b) by 22 days.

(21) Appl. No.: 12/316,453

(22) Filed: Dec. 12, 2008

(51) Int. Cl.
*A01H 5/00* (2006.01)

(52) U.S. Cl. ..... Plt./331

(58) Field of Classification Search ..... Plt./331
See application file for complete search history.

(56) References Cited

OTHER PUBLICATIONS

UPOV ROM GTITM Computer Database, GTI Jouve Retrieval Software 2009/04 Citation for 'Elegance Purple Majesty'.*

* cited by examiner

*Primary Examiner*—Wendy C. Haas
(74) *Attorney, Agent, or Firm*—C.A. Whealy

(57) ABSTRACT

A new and distinct cultivar of Regal *Geranium* plant named 'Oglreg3067', characterized by its upright and mounded plant habit; freely branching habit; freely flowering habit; relatively small leaves; and large light violet and purple bi-colored flowers.

1 Drawing Sheet

Botanical designation: *Pelargonium×domesticum.*
Cultivar denomination: 'OGLREG3067'.

BACKGROUND OF THE INVENTION

The present invention relates to a new and distinct cultivar of Regal *Geranium* plant, botanically known as *Pelargonium×domesticum*, and hereinafter referred to by the name 'Oglreg3067'.

The new Regal *Geranium* plant is a product of a planned breeding program conducted by the Inventor in Lompoc, Calif. The objective of the breeding program is to create new compact and early and freely flowering Regal *Geranium* cultivars with large and attractive flowers.

The new Regal *Geranium* plant originated from a cross-pollination made by the Inventor in March, 2000 in Lompoc, Calif. of a proprietary selection of *Pelargonium×domesticum* identified as code number 10041, not patented, as the female, or seed, parent with a proprietary selection of *Pelargonium×domesticum* identified as code number 9997, not patented, as the male, or pollen, parent. The new Regal *Geranium* was discovered and selected by the Inventor as a single flowering plant from within the progeny of the stated cross-pollination in a controlled greenhouse environment in Lompoc, Calif. in March, 2001.

Asexual reproduction of the new Regal *Geranium* plant by vegetative terminal cuttings in a controlled greenhouse environment in Connellsville, Pa. since May, 2002, has shown that the unique features of this new Regal *Geranium* plant are stable and reproduced true to type in successive generations.

SUMMARY OF THE INVENTION

Plants of the new Regal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Oglreg3067'. These characteristics in combination distinguish 'Oglreg3067' as a new and distinct cultivar of Regal *Geranium:*

1. Upright and mounded plant habit.
2. Freely branching habit.
3. Freely flowering habit.
4. Relatively small leaves.
5. Large light violet and purple bi-colored flowers.

Plants of the new Regal *Geranium* differ primarily from plants of the female parent selection in flowering habit as plants of the new Regal *Geranium* flower earlier and more freely than plants of the female parent selection.

Plants of the new Regal *Geranium* differ primarily from plants of the male parent selection in growth and flowering habit as plants of the new Regal *Geranium* are more freely branching and more freely flowering than plants of the male parent selection.

Plants of the new Regal *Geranium* can be compared to plants of *Pelargonium×domesticum* 'Jewel', disclosed in U.S. Plant Pat. No. 13,519. In side-by-side comparisons conducted in Encinitas, Calif., plants of the new Regal *Geranium* differed primarily from plants of 'Jewel' in the following characteristics:

1. Plants of the new Regal *Geranium* were more freely flowering than plants of 'Jewel'.
2. Plants of the new Regal *Geranium* and 'Jewel' differed in flower color as plants of 'Jewel' had white and red purple bi-colored flowers.

BRIEF DESCRIPTION OF THE PHOTOGRAPHS

The accompanying colored photographs illustrate the overall appearance of the new Regal *Geranium* plant, showing the colors as true as it is reasonably possible to obtain in colored reproductions of this type. Colors in the photographs may differ slightly from the color values cited in the detailed botanical description which accurately describe the colors of the new Regal *Geranium* plant.

The photograph at the bottom of the sheet comprises a side perspective view of a typical flowering plant of 'Oglreg3067' grown in a container.

The photograph at the top of the sheet is a close-up view of typical flowers and leaves of 'Oglreg3067'.

DETAILED BOTANICAL DESCRIPTION

The aforementioned photographs and following observations, measurements and values describe plants grown in Encinitas, Calif. in a plastic-covered greenhouse during the spring and under conditions which closely approximate Regal *Geranium* commercial production. During the production of the plants, day temperatures averaged 24° C., night temperatures averaged 19° C. and light levels averaged 4,000 foot-candles. Plants had been growing for 13 weeks when the photographs and the description were taken. In the detailed description, color references are made to The Royal Horticultural Society Colour Chart, 2001 Edition, except where general terms of ordinary dictionary significance are used.

Botanical classification: *Pelargonium×domesticum* 'Oglreg3067'.

Parentage:

*Female, or seed, parent.*—Proprietary selection of *Pelargonium×domesticum* identified as code number 10041, not patented.

*Male or pollen parent.*—Proprietary selection of *Pelargonium×domesticum* identified as code number 9997, not patented.

Propagation:

*Type.*—By vegetative terminal cuttings.

*Time to initiate roots, summer.*—About 35 days at temperatures of 21° C.

*Time to initiate roots, winter.*—About 40 days at temperatures of 18° C.

*Time to produce a rooted young plant, summer.*—About 70 days at temperatures of 24° C.

*Time to produce a rooted young plant, winter.*—About 80 days at temperatures of 18° C.

*Root description.*—Medium in thickness, fleshy; white in color.

*Rooting habit.*—Moderate branching; moderately dense.

Plant description:

*General appearance.*—Upright and mounding plant habit; densely foliated.

*Growth and branching habit.*—Moderately vigorous to vigorous growth habit. Freely branching habit; about eight primary lateral branches develop per plant.

*Plant height, to top of foliar plane.*—About 17 cm.

*Plant height, to top of umbels.*—About 28 cm.

*Plant diameter (spread).*—About 24 cm.

*Lateral branches.*—Length: About 15 cm. Diameter: About 5 mm. Internode length: About 1.6 cm. Texture: Pilose. Strength: Strong, stiff. Color: Close to 144A.

Foliage description:

*Arrangement.*—Alternate; simple.

*Length.*—About 6.3 cm.

*Width.*—About 6.9 cm.

*Shape.*—Reniform to broadly cordate.

*Apex.*—Acute to acuminate.

*Base.*—Cordate.

*Margin.*—Biserrate; crinkled, sinuous.

*Venation pattern.*—Palmate.

*Texture, upper and lower surfaces.*—Pubescent.

*Color.*—Developing leaves, upper surface: Close to 146B. Developing leaves, lower surface: Close to 146C. Fully expanded leaves, upper surface: Close to 146A; venation, close to 146B. Fully expanded leaves, lower surface: Close to 147B; venation, close to 147C.

*Petiole.*—Length: About 4.8 cm. Diameter: About 2 mm. Texture, upper and lower surfaces: Smooth, glabrous. Color, upper and lower surfaces: Close to 147B.

Flower description:

*Flower arrangement.*—Nearly round flowers arranged in hemispherical and loose umbels arising from apical leaf axils. Umbels displayed above the foliage on strong peduncles. Flowers face upright to outward; flowers slightly cupped becoming flatter with development and apices recurving.

*Fragrance.*—None detected.

*Quantity of flowers.*—Freely flowering habit; about eight flowers per umbel; about five developed umbels per plant at one time.

*Flowering season.*—In Encinitas, Calif., flowering is continuous during the spring and early summer.

*Flower longevity.*—Individual flowers last about one week on the plant; flowers not persistent.

*Umbel height.*—About 5.2 cm.

*Umbel diameter.*—About 7.5 cm.

*Flower diameter.*—About 4.5 cm.

*Flower depth (height).*—About 3 cm.

*Flower buds.*—Length: About 2.7 cm. Diameter: About 1.1 cm. Shape: Elliptical. Color: Close to 84C.

*Petals.*—Quantity per flower: Five in a single whorl. Length: About 2.8 cm to 3.2 cm. Width: About 1.8 cm to 2.5 cm. Shape: Obovate. Apex: Rounded. Base: Attenuate. Margin: Sinuate. Texture, upper and lower surfaces: Smooth, glabrous; velvety. Color: When opening, upper and lower petals, upper surface: Close to 76B to 76C. When opening, upper and lower petals, lower surface: Close to 76C to 76D. Fully opened, upper petals, upper surface: Close to 84C; central splotch, close to N79B; towards the base, close to NN155D; venation, close to N79B; color does not fade with development. Fully opened, lower petals, upper surface: Close to 84C; towards the base, close to NN155D; venation, close to 84C; color does not fade with development. Fully opened, upper petals, lower surface: Close to 84D; central splotch, close to N79C; at the base, close to NN155D; venation, close to N79C. Fully opened, lower petals, lower surface: Close to 84D; at the base, close to NN155D; venation, close to 84D.

*Sepals.*—Quantity per flower: Five, arranged in a single whorl. Length: About 1.5 cm. Width: About 4 mm to 5 mm. Shape: Narrowly elliptical. Apex: Acuminate. Base: Attenuate. Margin: Entire. Texture, upper and lower surfaces: Pilose. Color, upper surface: Close to 146C. Color, lower surface: Close to 146B.

*Peduncle (umbel stem).*—Length: About 5.6 cm. Diameter: About 2.5 mm. Strength: Strong. Texture: Pubescent. Color: Close to 147B.

*Pedicel* (*individual flower stem*).—Length: About 2.2 cm. Diameter: About 1 mm. Strength: Strong. Texture: Pubescent. Color: Close to 146C.

*Reproductive organs.*—Androecium: Stamen quantity per flower: About eight. Anther size: About 1 mm by 2 mm. Anther shape: Narrowly oblong. Anther color: Close to 181D. Pollen amount: None observed. Gynoecium: Pistil quantity per flower: One. Pistil length: About 1.7 cm. Stigma shape: Split into five to seven parts, star-shaped. Stigma color: Close to 187A. Style length: About 8 mm. Style color: Close to 187B. Ovary color: Close to 190A.

*Seed/fruit.*—Seed and fruit development have not been observed.

Disease/pest resistance: Plants of the new Regal *Geranium* have not been observed to be resistant to pathogens and pests common to Regal *Geraniums*.

Temperature tolerance: Plants of the new Regal *Geranium* have been observed to tolerate temperatures ranging from about 2° C. to about 35° C.

It is claimed:

1. A new and distinct Regal *Geranium* plant named 'Oglreg3067' as illustrated and described.

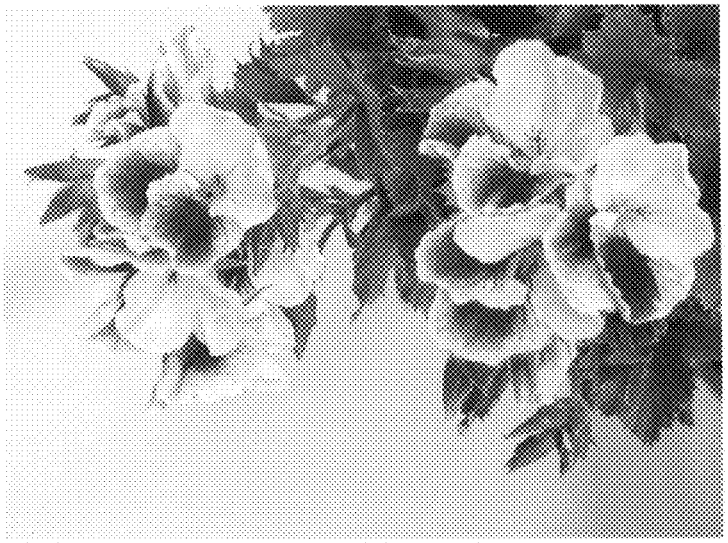
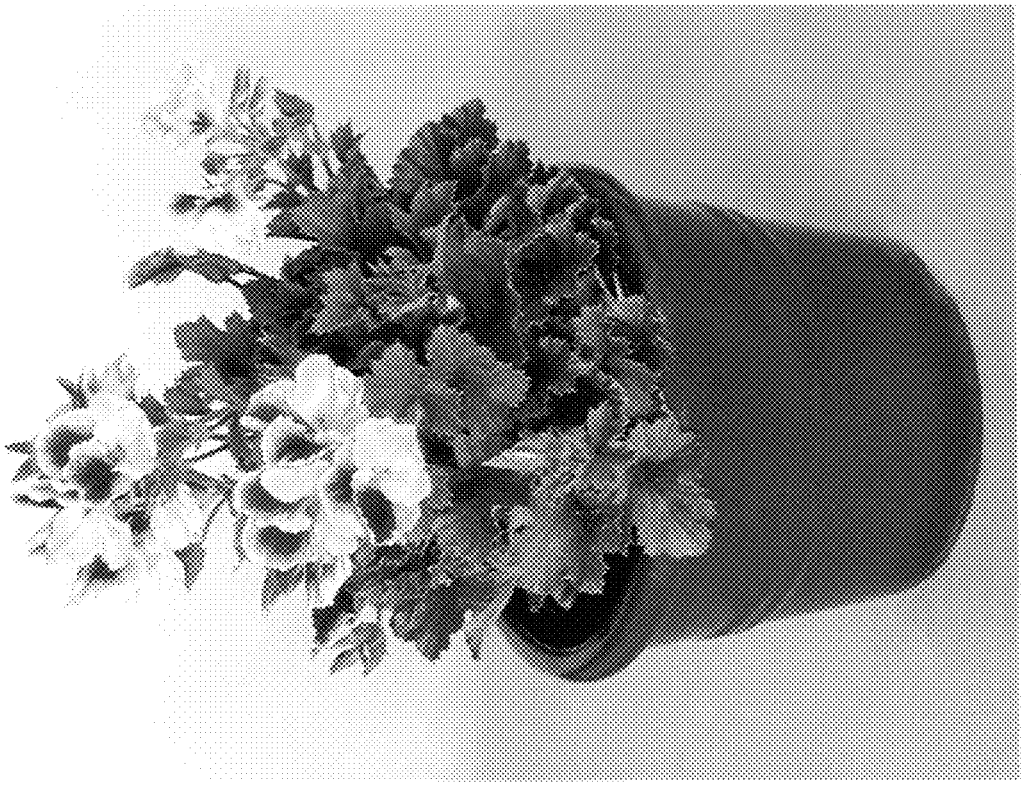

* * * * *